US006177522B1

(12) United States Patent
Brady et al.

(10) Patent No.: US 6,177,522 B1
(45) Date of Patent: Jan. 23, 2001

(54) BIOSTABLE POLYCARBONATE URETHANE PRODUCTS

(75) Inventors: Eamon Brady, Elphin; Fergal Farrell, Athy, both of (IE)

(73) Assignee: Salviac Limited, Dublin (IE)

( * ) Notice: Under 35 U.S.C. 154(b), the term of this patent shall be extended for 0 days.

(21) Appl. No.: 09/188,474

(22) Filed: Nov. 9, 1998

(30) Foreign Application Priority Data

Nov. 7, 1997 (IE) .......................................... 970790
Apr. 2, 1998 (IE) .......................................... 980240

(51) Int. Cl.[7] ................................................. C08G 18/00
(52) U.S. Cl. ........................ 525/452; 528/196; 528/198; 528/201
(58) Field of Search .................................. 528/196, 198, 528/201; 525/452

(56) References Cited

U.S. PATENT DOCUMENTS 5,254,662  10/1993  Szycher .................................. 528/67
5,621,065   4/1997  Pudlinier .............................. 528/84

FOREIGN PATENT DOCUMENTS 0 461 375 A1   12/1991   (EP) .

OTHER PUBLICATIONS

George Woods, I.C.I. Polyurethane Handbook (2nd Edition John Wiley and sons). (1990).

*Primary Examiner*—Terressa M. Boykin
(74) *Attorney, Agent, or Firm*—Finnegan, Henderson, Farabow, Garrett & Dunner, L.L.P.

(57) ABSTRACT

Porous and non-porous polycarbonate urethane polymers having a set of properties suitable for long term implantation within the body of a mammal. The polycarbonate foams and elastomers, comprise a polycarbonate material that is resistant to attack by invivo agents over extended periods of time. The polycarbonate urethane polymers are prepared by reacting polycarbonate polyols with an isocyanate and a chain extender.

29 Claims, No Drawings

BIOSTABLE POLYCARBONATE URETHANE PRODUCTS

The invention relates to biostable polycarbonate urethane and polycarbonate urethane urea products.

This invention relates to porous and nonporous polycarbonate urethane (PCU) polymers having a set of properties which make then suitable for long term implantation within a living human body. The polyurethane foams and elastomers of this invention comprise a PCU material that is resistant to attack by in vivo agents over extended periods of time.

BACKGROUND OF THE INVENTION

There are a series of commercially available polyurethane materials which are suitable for the manufacture of implantable medical devices. Typically these materials combine good elasticity, ultimate tensile strength, biocompatibility and biostability. However, only a small percentage of the spectrum of commercially available polyurethanes are suitable for implantation. Those that are suitable for implantation are typically based on a polyether or polycarbonate macroglycol together with a diisocyanate and a diol or diamine chain extender. Examples of these are described in EP Patent No. 461,375 (Pinchuck) and U.S. Pat. No. 5,621,065 (Pudlinear et al).

Products manufactured from conventional polyurethane materials are processed in two stages. Firstly the macroglycol, the diisocyanate and the chain extender are reacted in specific molar ratios so as to produce a polymer with a linear molecular structure. These systems are subsequently processed by any of a variety of thermomechanical or solvent based processes into geometry's suitable for implantation. Polyurethane polymers with a linear molecular structure lend themselves to processing by these techniques. Polyurethanes with three dimensional molecular structures do not lend themselves to processing by either thermomechanical or solvent techniques, rather these materials must be formed into useful articles as part of the polymerisation reaction.

The chemistry and materials of polyurethane manufacture are well known to those skilled in the art and are described in many publications such as the I.C.I. Polyurethane Handbook by George Woods ($2^{nd}$ Edition John Wiley & Sons).

Most currently available polyurethane materials are chain extended using a diol or a diamine. Diols react with the isocyanate linkage to generate urethane groups whereas amines react with isocyanates to generate urea linkages. Water can also be employed as a chain extender as it reacts with two isocyanate groups to form a urea linkage and gives off carbon dioxide in the process. The hard segment generated with water chain extenders has a high concentration of urea linkage and is thus stiff and polar. Water however is little used for chain extending biomedical polyurethanes as it generates carbon dioxide in the reaction. The inclusion of water is considered to be undesirable.

Linear polymers may be processed by either thermomechanical or solution processes. Polyurethanes with a high urea content are normally difficult to process thermomechanically and are usually solution processed. As most conventional polyurethanes are processed thermomechanically, by processes like extrusion and injection moulding, most conventional polyurethanes do not have high concentrations of urea linkages. Conventional polyurethanes are thus normally chain extended using short chain diols.

Polycarbonate based polyols have been used in the manufacture of polyurethane elastomers as described in U.S. Pat. No. 5,254,662 (Szycher), where the polycarbonates are represented by the following general formula $$HO(R_1O(CO)OR_1)_nOH$$

$R_1$ represents an aliphatic chain of from 2 to 20 carbon atoms, and n has a value sufficient to generate a molecular weight of from 650 to 3500 molecular weight units. The main difficulty with systems based on these polycarbonates is generating a material that is sufficiently soft and elastomeric for implantation in a soft tissue environment. This issue arises due to the regularity of the polycarbonate polyol structure.

The repeat unit of a typical polyol of the form shown above could be represented as follows:

$$(CH_2CH_2CH_2CH_2CH_2CH_2O{-}CO{-}O)$$

The oxygens of the carbonate linkage are more electron withdrawing than the carbons to which they are bonded. The oxygens therefore carry a slight negative charge while the carbons carry a slightly positive charge. When carbonate linkages of neighbouring chains come into close proximity the positive charges of one chain will interact in an attractive fashion with the negative charges of the other chain. The chain structure of the carbonates employed in U.S. Pat. No. 5,524,662 (Szycher) and similarly in EP 461375 (Pinchuck) contains linkages that allow the chain to take up a linear configuration. These chains containing no side groups to disrupt the regularity of the structure. These features allow the attractive forces associated with the carbonate linkage to dominate the stiffness of the polyol phase. This attraction significantly increases the stiffness characteristics of resulting PCU. The greater the concentration of carbonate linkages in this type of regular polyol phase the stiffer the resulting polyurethane will be.

The C—O linkage of the carbonate oxygen and carbon of the hydrocarbon chain could however have a low energy of rotation. This low energy of rotation should have the effect of softening the polyol phase. This is not observed to be the case because the attractive forces between the carbonates lock these rotational movements in and prevent these movements from having a significant influence on the material softness. Because polycarbonates of the type employed by Szycher and Pinchuck are very regular in structure they generate polyurethanes that are much stiffer than comparative polyether urethanes.

It is an object of the present invention to provide soft, flexible polycarbonate urethane polymers having properties making them suitable for long term implantation.

SUMMARY OF THE INVENTION

The biostable polycarbonate urethane article of this invention is made from a polycarbonate urethane prepared by the reaction of an isocyanate, a polycarbonate and a chain extender, such that the polycarbonate is a polycarbonate copolymer polyol of alkyl carbonates.

The biostable polyurethane devices of this invention are derived from organic diisocyanates and polycarbonate copolymer polyols and are chain extended with either diamine, diol, alkanol amine, water or mixtures of the above chain extenders. The reaction step converts the chemical precursors into a polymer of high molecular weight while the forming step shapes the article into the desired geometry.

Preferably, the polycarbonate copolymer polyol is a random copolymer of alkyl carbonates.

The use of random copolymers affects the bonding properties of the carbonate linkages. Hence, the polycarbonate copolymer polyols used in the manufacture of polyurethanes of this invention are designed to prevent significant interaction between neighbouring polyol chains and also to permit free rotation about the C—O bond of the carbonate oxygen and the hydrocarbon sequence. This reduces the stiffness of the material.

Most preferably the length of the alkyl chains in the alkyl carbonates varies between 2 to 16 carbon atoms.

In another embodiment, the article is made from a polycarbonate urethane comprising a polymeric molecular structure having recurring carbonate groups in combination with one or both of urea and urethane and biuret groups when urea is present and allophanate when urethane is present to form a 3-dimensional polymer molecular structure.

The isocyanates react under suitable conditions with the active hydrogens of the urethane and urea linkages to form biuret and allophanate linkages. These linkages represent points of trifurcation in the molecular structure and confer a 3-dimensional structure to the resultant polyurethane article. This 3-dimensional structure within the article, bestows the properties of high compressibility and high recoverability.

In a preferred embodiment, the isocyanate can be selected from one or more of the group of aliphatic, aliphatic alicyclic, aromatic, aromatic-aliphatic diisocyanates and tri-isocyanates.

Preferably, the isocyanate is represented by the formula

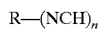
R—(NCH)$_n$ wherein R is an aliphatic, aromatic, cycloaliphatic, or an aliphatic aromatic hydrocarbon entity containing between 4 and 24 carbon atoms and n is greater than 1.85. Most preferably, n varies from between 1.9 and 2.2.

In another embodiment, the isocyanate is selected from one or more of p-phenylene diisocyanate, tetramethylene diisocyanate, cyclohexane 1,2-diisocyanate, m-tetramethylxylene diisocyanate, hexamethylene diisocyanate, diphenylmethane diisocyanate, 2,4 toluene diisocyanate, 2,6 toluene diisocyanate, cyclohexane 1,4 diisocyanate, isophorone diisocyanate, 4,4-dicyclohexylmethane diisocyanate and triisocyanates.

In another embodiment, the chain extender is selected from one or more of a diol, a diamine, an alkanol amine and water.

Preferably, the chain extender is an aliphatic diol, and has from 2 to 10 carbon atoms, and is chosen from one or more of ethylene glycol, 1,4 butanediol, diethylene glycol, triethylene glycol, 1,2 propane diol, 1,3 propane diol, 1,5 pentane diol and isomers of the above.

The choice of an aliphatic diol to chain extender results in the production of a softer material.

In another embodiment, the chain extender is an aliphatic diamine having 2 to 10 carbons and is chosen from one or more of ethylene diamine, 1,4 diaminobutane, 1,6 diaminohexane, 1,7 diaminoheptane, 1,8 diaminooctane and 1,5 diaminopentane.

In another embodiment, the chain extender is an aliphatic alkanol amine having from 2 to 10 carbon atoms.

Preferably, the density of the article is in the range of 20 kg/m$^3$ to 1300 kg/m$^3$. Most preferably, less than 250 kg/m$^3$.

In another embodiment, the article has a percentage void space of at least 70%. Preferably, at least 80%.

By producing an article with such high percentage void space produces an article with a cellular structure.

In another embodiment, the biostable polycarbonate urethane article of the present invention is made from a polycarbonate urethane comprising:

a polymeric molecular structure having recurring carbonate groups in combination with one or both of urea and urethane and biuret groups when urea present and allophanate when urethane present to form a 3-dimensional polymer molecular structure.

said polymer being a reactant product of a polycarbonate polyol, an isocyanate and a chain extender.

Hence, useful polyurethane articles of this invention may be of a three dimensional molecular structure.

In another embodiment, the isocyanate is represented by the formula

R—(NCO)$_n$ and n is greater than 2.

According to the present invention, a method of making a biostable polycarbonate foam article is provided comprising simultaneously reacting a polycarbonate polyol, an isocyanate and water.

The reaction of the isocyanate with water yields carbon dioxide. This provides a source of gas for blowing in the manufacture of low density flexible foams.

Preferably, the process is a reaction forming process.

Most preferably, the process is carried out under depressurised or vacuum conditions. This facilities maximum expansion from a given concentration of blowing agent.

In a preferred embodiment, the reaction ingredients are degassed under vacuum or otherwise prior to reaction. This ensures that the pores formed are homogenous in size.

In a preferred embodiment, the process is a reactive blow moulding process with aggressive mixing of the reactants while injecting into a mould.

Thus the structure and geometry are formed simultaneously under stress free conditions. The aggressive mixing ensures that the pores are homogeneously distributed. By manufacturing the article under stress free conditions, the resultant product is thus very resilient when utilised under conditions of stress such as when placed within the body of a mammal for extended periods, when no degradation of the product is required.

In another embodiment, additional volatile solvents are added to the reactants and in another embodiment a solubilised gas such as carbon dioxide is added to the reactants.

These also provide an alternative source of gas for blowing. These gases can be employed to expand the physical structure and generate a porous structure though a controlled blowing process.

In another embodiment, the isocyanate is represented by the formula

R—(NCO)$_n$ and n varies from between 2 and 3.

Preferably, biostable polycarbonate urethane article when manufacture in accordance with the method described.

In a preferred embodiment, the foam is first formed into a block for subsequent cutting to a desired shape. Thus, the foam manufacture is an ideal material for use as an implant to occlude vessels. It provides a product which is non-abrasive whilst resilient, has dynamic properties, is expandable and is self supporting. Its porous nature provides a cellular open structure which allows tissue infiltration. Furthermore, it is collapsible and highly compressible.

The biostable polycarbonate urethane article according to the present invention is useful in the manufacture of vascular grafts, septal defect occluders, vessel occluders, vessel defect occluders, mammary prosthesis, pacemaker leads, embolic filters, LVAD bladders, probes, cannulas, or catheters and other such implant and blood contacting devices.

DETAILED DESCRIPTION OF THE INVENTION

The present invention described a range of polycarbonate urethane biomaterials suitable for long-term human implantation and processes for the manufacture of useful medical devices from such a material. This invention deals with materials that are intended for applications requiring porosity and for applications that require non-porous structures. The biostable polyurethanes of this invention are based on organic diisocyanates, polycarbonate copolymer polyols and diol, diamine, alkanol, amine or water chain extenders.

The polyurethane of this invention are based on organic diisocyanates of the general formula:

$$R-(NCO)_n$$

Where R is an aliphatic, aromatic, cycloaliphatic, or an aliphatic-aromatic hydrocarbon entity containing between 4 and 24 carbon atoms and n is greater than 1. More preferably R contains between 4 and 13 carbon atoms. Where n is 2 a polymer with a linear molecular structure may be produced. A three dimensional molecular network may be produced where n varies from 2 to 3. Ideally n should be 2. A 3-dimensional molecular structure can be generated where n=2 is the isocyanate is used in excess.

Examples of suitable isocyanates include: p-phenylene diisocyanate, tetramethylene diisocyanate, cyclohexane 1,2-diisocyanate, m-tetramethylxylene diisocyanate, hexamethylene diisocyanate, diphenylmethane diisocyanate, 2,4 toluene diisocyanate, 2,6 toluene diisocyanate, cyclohexane 1,4 diisocyanate, isophorone diisocyanate, 4,4-dicyclohexylmethane diisocyanate, 4,4-dicyclohexylmethane diisocyanate, mixtures of the above mixtures of the above with atriisocyanate.

Where secondary chain extenders are employed, these can be either amine or diols. Most diols, diamines or alkanol amines make suitable chain extenders.

Aliphatic diol chain extenders having 2 to 10 carbon atoms can be represented by the formula $$HO-R-OH$$

where R is an aliphatic group containing from 2 to 10 carbon atoms. Examples of aliphatic diols are ethylene glycol, 1,4 butane diol, diethylene glycol, triethylene glycol, 1,2 propane diol, 1,3 propane diol, 1,5 tentane diol, isomers of the above or mixtures thereof.

Aliphatic diamine chain extenders can be represented by the formula $$H_2N-R-NH_2$$

where R is an aliphatic group containing from 2 to 10 carbon atoms. Examples of aliphatic diamine chain extenders include ethylene diamine, 1,4 diaminobutane, 1,6 diaminohexane, 1,7 diaminoheptane, 1,8 diaminooctane, 1,5 diaminopentane or mixtures thereof.

Polyether based polyurethanes can be designed to be much softer than those of their carbonate counterparts for the following reasons:

Polyethers do not have the same attractive forces between the chains.

The energy of rotation about the C—O (ether) linkage is lower even than the energy of rotation about the C—C linkage and this reduces the stiffness of the material.

Thus, it would be advantageous to have a polycarbonate urethane with similar properties.

The polyurethanes of this invention are manufactured from polycarbonate copolymer polyols. These polyols are ideally random copolymers and cannot be accurately represented by a generalised formula. However, a copolymer polyol wherein there are two types of alkyl chains is represented below:

$$HO-(CH_2)_xO(CO)O(CH_2)_yO(CO)O(CH_2)_xO(CO)O(CH_2)_x$$
$$O(CO)O(CH_2)_yO(CO)-OH$$

Wherein the alkyl sequences denoted by x and y occur randomly along the chain. The concentration of the x and y alkyl sequences can vary considerably. For given values of x and y values which permit the most randomisation of the carbonate linkages are desirable.

A polycarbonate copolymer polyol with three alkyl sequences is represented below.

$$HO-(CH_2)_xO(CO)O(CH_2)_yO(CO)O(CH_2)_z$$
$$O(CO)O(CH_2)_yO(CO)O(CH_2)_xO(CO)-OH$$

It is equally possible to have carbonate copolymer polyols wherein there are multiple different alkyl sequences. These systems would be employed to achieve the greatest levels of randomisation.

These polycarbonate polyols are employed as they overcome the limitations of conventional polycarbonate polyols. As stated above, the difficulties associated with conventional polycarbonate polyols arises from the following characteristics:

There are strong attractive forces between carbonate linkages of neighbouring chains.

The chain is linear, regular and contains no side groups and this allows the chains to get sufficiently close for these attractive forces to act.

The chain length between carbonate is constant thus all carbonates on one chain may interact with all carbonates of its neighbour.

The attractive forces prevent rotations about the C—O bond of the carbonate oxygen and the carbon of the hydrocarbon chain.

The polycarbonate copolymer polyols employed in the manufacture of articles of this invention are manufactured by a number of different methods. The most common approach to the formation of these materials involves the reaction of two or more different diols with a carbonate monomer. The length of the hydrocarbon chain between neighbouring carbonates will be the same as the length of the hydrocarbon chain of the original diol which reacted at that site. A simplified reaction sequence is shown in example 1.

EXAMPLE 1

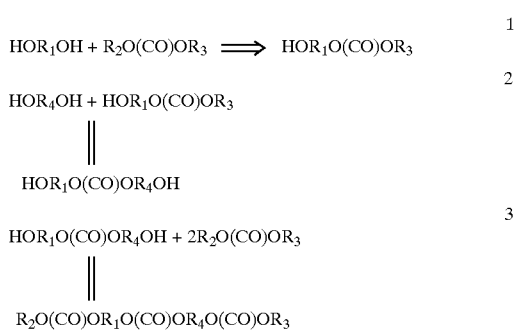

-continued

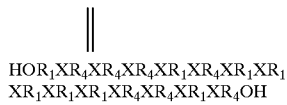

Where, $R_1$, $R_2$, $R_3$, and $R_4$ are hydrocarbon chains, and X is an abbreviation for the carbonate linkage.

The use of two or more diols in the polycarbonate formation reaction has the following general effects when these polyols are incorporated into the polyurethanes of this invention:

The chain length between carbonates varies along the length of the chain. This makes it impossible for all carbonates of one chain to interact with all carbonates of its neighbour. It is possible for a percentage of the carbonate linkages to interact. The percentage of carbonates that interact depends on the chain lengths of the original diols and the ratio of these in the material.

The bond angle of a C—C—C series of linkages will be different to that of the O—C—O series of the carbonate linkage. This bond angle difference does not cause molecular structure disruption in conventional polycarbonate urethanes because it occurs regularly along the chain. However this effect becomes more important when the carbonate linkage occurs at irregular intervals along the chain. In this situation, the difference in bond angles may have the effect of increasing chain separation and making it more difficult for neighbouring chains to pack close together and form dispersion or polar bonds.

Chain separation may be increased by the use of diols with side groups in their structure. These side groups will make it more difficult for the chains to pack close together and this will make it difficult for the carbonate linkages of neighbouring chains to interact. The incorporation of side groups should enhance flexibility. It is a less desirable characteristic for long-term biostability as the tertiary carbon is a potential point of oxidative attack. This effect may be overcome by providing steric hindrance at this site.

The disruption of the carbonate linkages will also have the effect of freeing the rotations about the oxygen of the carbonate linkage and the carbon of the hydrocarbon chain. This will also improve the softness of the resulting polycarbonate urethane articles.

EXAMPLE 2

If the copolymer has two chain repeat units of C4 and C6 then two neighbouring chains might adopt the following configuration:

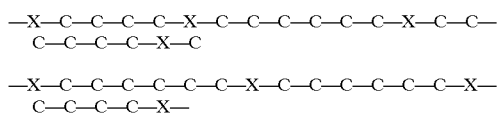

Where X represents a carbonate linkage and C represents a linkage on a hydrocarbon chain. C4 and C6 represent methylene sequences of four and six carbons respectively.

From example 2 is it clear that approximately 50% of the carbonate linkages are in positions which facilitate interaction. This will significantly improve the softness of the material when compared to a conventional C6 polycarbonate. If it is desired to make the polymer even more flexible then different repeat units may be employed. If for example a C6 was employed in conjunction with a C7 or a C10 then the percentage of interactions might be significantly reduced. Even is the C4 and C6 are employed in ratios other than 50:50 a significant difference in softness can be achieved. It should thus be obvious that at a given carbonate linkage concentration it is possible to make polycarbonate urethanes with vastly different softness/stiffness characteristics without the need to change the molecular weight of the polymer or the hard segment content.

The polycarbonate urethanes of this invention are based on diol, diamine, alkanolamine, water chain extenders or mixtures of these. Diol chain extenders react with isocyanate to generate urethane linkages. Diamine and water generate urea linkages and alkanol amines can generate both urethane and urea linkages. The use of water as a chain extender in biomedical polyurethanes is unusual as with most conventional biomedical polyurethanes water is viewed as an impurity. The water chain extension reactions generate urea linkages in the hard segment and carbon dioxide is given off as a by product. The presence of significant quantities of urea linkages in the hard segment has the following important effects:

Polyurea's in the hard segment generate significant levels of hydrogen bonding that causes the hard segment to be strong and this adds to the ultimate properties of the material.

It also promotes phase separation of the hard isocyanate/chain extender phase and the soft polyol phase. Phase separation is beneficial to the elastomeric and biocompatibility properties of the material.

The presence of significant concentrations of urea linkages in the hard segment makes linear polyurethanes difficult to process by thermomechanical techniques.

The carbon dioxide generated from the water isocyanate reaction series can be used to influence the density of the material by generating a cellular structure.

Polyurethanes with a high concentration of urea linkages in the hard phase tend to be strong elastomers with good flex lives. The carbon dioxide generated as a by product of the isocyanate-water-isocyanate reaction series can be employed to generate a cell structure in the material. With the use of a surfactant the size and porosity of this cell structure can be controlled. The level of water used in the reaction determines the amount of carbon dioxide generated and the hard segment content of the polymer. The amount of carbon dioxide generated plays an important role in the density of the polyurethane. By this invention the density can be controlled independently of the hard segment content by controlling the pressure of the reaction/forming chamber. Thus biostable polyurethanes of this invention can be manufactured with densities ranging from 30 kg/m³ to 1200 kg/m³ virtually independent of the hard segment content.

The polymerisation of biostable polyurethanes of this invention involves the reaction of —OH groups from the polyol with —NCO groups from the diisocyanates to form urethane linkages. These chemical groups are reacted in approximately equivalent ratios for the generation of linear polymers and with a slight excess for a crosslinked (three dimensional) molecular structure.

For the generation of biostable foams water is used as the primary chain extender. Secondary chain extenders may be employed to alter the hard segment content or to alter specific properties. Manufacturing foams of the lowest densities per this invention is carried out by a combination of water blown reaction, in a depressurised reactive/forming vessel with the incorporation of a physical blowing agent into the formulation. Secondary chain extenders can be either diamine, diol or alkanol amine based and should have a functionality of two or greater. Diol chain extenders are preferred.

Most diols or diamines make suitable chain extenders. Examples of such chain extenders include, ethylene glycol, 1,4 butanediol, diethylene glycol, triethylene glycol, 1,2 propane diol, 1,3 propane diol, 1,5 pentane diol, ethylene diamine, 1,4 diaminobutane, 1,6 diaminohexane, 1,7 diaminoheptane, 1,8 diaminooctane, and 1,5 diaminopentane.

Biostable articles of this invention can be chemically prepared by the following methods:

The one shot process in which the diisocyanate, the polyol and the chain extender are mixed and reacted in one step.

The prepolymer method wherein an isocyanate-terminated prepolymer is first prepared and then the system is chain extended.

The quasiprepolymer system wherein some of the polyol is reacted with the isocyanate to generate an isocyanate terminated prepolymer in an excess of isocyanate. The remaining polyol and chain extender is subsequently added and facilitates chain extension.

Biostable articles of this invention may be processed by any of the following techniques:

Reactive blow moulding process, wherein the chemical ingredients are aggressively mixed and dispensed into a mould and chain extension and blowing reactions occur simultaneously. This process is suitable for the manufacture of a three dimensional molecular structure and is suited to the manufacture of low-density porous and non-porous articles.

Reactive moulding process, wherein the chemical ingredients are mixed and dispensed into a mould wherein chain extension occurs. This process if primarily suitable for the manufacture of a three dimensional molecular structure and is suited to the manufacture of solid biostable articles.

A reactive process wherein the number of isocyanate linkages in the reaction vessel is approximately equal to the number of active hydrogens in the vessel. This process is suitable for the manufacture of polycarbonate urethanes with a linear molecular structure. These materials can then be processed by a variety of standard thermomechanical and solvent based processes.

Reactive blowing process, wherein the chemical ingredients are aggressively mixed and dispensed in a continuous fashion and expand and chain extend simultaneously to form a continuous block of foam which is subsequently cut or machined into useful shapes. This process is suitable for the manufacture of a three dimensional molecular structure and is suited to the manufacture of low-density porous and non-porous articles.

The invention is not limited to the embodiments hereinbefore described which may be varied in detail.

We claim:

1. A biostable polycarbonate urethane article of the type in which the article is made from a polycarbonate urethane as prepared by the reaction of an isocyanate, a polycarbonate and a chain extender, characterized in that:

the polycarbonate is a polycarbonate copolymer polyol of carbonate linkages connected with alkyl sequences;

the polycarbonate copolymer polyol is formed through the reaction of two or more different diols with a carbonate monomer; and the diols being chosen such that there are two or more different alkyl sequences which are positioned randomly between the carbonate linkages of the chain and the length of each alkyl sequence is from 3 to 16 carbon atoms.

2. A biostable polycarbonate urethane article as claimed in claim 1, wherein the polycarbonate copolymer polyol is represented by the following generalized formula:

$$HO-(CH_2)_xO(CO)O(CH_2)_yO(CO)O(CH_2)_xO(CO)O(CH_2)_xO(CO)O(CH_2)_yO(CO)-OH$$

3. A biostable polycarbonate urethane article as claimed in claim 1, wherein the polycarbonate copolymer polyol is represented by the following generalized formula:

$$HO-(CH_2)_xO(CO)O(CH_2)_xO(CO)O(CH_2)_z O(CO)O(CH_2)_yO(CO)O(CH_2)_xO(CO)o-OH$$

4. A biostable polycarbonate urethane article as claimed in claim 1, wherein the isocyanate is represented by the formula:

$$R-(NCO)_n$$

wherein R is an aliphatic, aromatic, cycloaliphatic, or an aliphatic-aromatic hydrocarbon entity containing between 4 and 24 carbon atoms and n is greater than or equal to 2.

5. A biostable polycarbonate urethane article as claimed in claim 1, wherein the article is made from a polycarbonate urethane comprising a polymeric molecular structure having recurring carbonate groups in combination with one or more of urea and urethane and biuret groups when urea is present and allophanate when urethane is present to form a 3-dimensional polymer molecular structure.

6. A biostable polycarbonate urethane article as claimed in claim 1, wherein the density of the article is less than 250 kg/m$^3$.

7. A biostable polycarbonate urethane article as claimed in claim 1, wherein the article has a percentage void space of at least 80%.

8. A biostable polycarbonate urethane article as claimed in claim 1, wherein the length of the alkyl chains in the carbonate linkages varies along the chain between 3 to 10 carbon atoms.

9. A biostable polycarbonate urethane article as claimed in claim 1, wherein the chain extender is selected from one or more of a diol, a diamine, an alkanol amine and water.

10. A biostable polycarbonate urethane article as claimed in claim 1, wherein the chain extender is water.

11. A biostable polycarbonate urethane article as claimed in claim 1, in which the chain extender is an aliphatic diol, and has from 2 to 10 carbon atoms.

12. A biostable polycarbonate urethane article as claimed in claim 1, in which the chain extender is an aliphatic diol chosen from one or more of ethylene glycol, 1,4 butanediol, diethylene glycol, triethylene glycol, 1,2-propane diol, 1,3 propane diol, 1,5 pentane diol and isomers of the above.

13. A biostable polycarbonate urethane article as claimed in claim 1, in which the chain extender is an aliphatic diamine having 2 to 10 carbons.

14. A biostable polycarbonate urethane article as claimed in claim 1, in which the chain extender is chosen from one or more of ethylene diamine, 1,4 diaminobutane, 1,6 diaminohexane, 1,7 diaminoheptane, 1,8 diaminooctane and 1,5 diaminopentane.

15. A biostable polycarbonate urethane article as claimed in claim 1, wherein the chain extender is an aliphatic alkanol amine having from 2 to 10 carbon atoms.

16. A biostable polycarbonate urethane article as claimed in claim 1, wherein the isocyanate can be selected from one or more of the group of aliphatic, aliphatic alicyclic, aromatic, aromatic-aliphatic diisocyanates and triisocyanates.

17. A biostable polycarbonate urethane article as claimed in claim 1, in which the isocyanate is selected from one or more of p-phenylene diisocyanate, tetramethylene diisocyanate, cyclohexane 1,2-diisocyanate, m-tetramethylxylene diisocyanate, hexamethylene diisocyanate, diphenylmethane diisocyanate, 2,4-toluene diisocyanate, 2,6-toluene diisocyanate, cyclohexane-1,4-diisocyanate, isophorone diisocyanate, 4,4-dicyclohexylmethane diisocyanate and triisocyanates.

18. A method of making a biostable polycarbonate foam article comprising simultaneously reacting a polycarbonate polyol, an isocyanate and water to yield carbon dioxide as a source for blowing said foam article, prepared by the reaction of an isocyanate, a polycarbonate and a chain extender, characterized in that:

the polycarbonate is a polycarbonate copolymer polyol of carbonate linkages connected with alkyl sequences;

the polycarbonate copolymer polyol is formed through the reaction of two or more different diols with a carbonate monomer; and the diols being chosen such that there are two or more different alkyl sequences which are positioned randomly between the carbonate linkages of the chain and the length of each alkyl sequence is from 3 to 16 carbon atoms.

19. A method of making a biostable polycarbonate foam article as claimed in claim 18, wherein the isocyanate is represented by the formula:

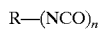

wherein R is an aliphatic, aromatic, cycloaliphatic, or an aliphatic-aromatic hydrocarbon entity containing between 4 and 24 carbon atoms and n is greater than or equal to 2.

20. A method of making a biostable polycarbonate foam article as claimed in claim 18, which is carried out under controlled pressure.

21. A method of making a biostable polycarbonate foam article as claimed in claim 18, which is carried out under a vacuum.

22. A method of making a biostable polycarbonate foam article as claimed in claim 18, including a reactive blow moulding method comprising mixing of the reactants while injecting the reactants into a mould.

23. A method of making a biostable polycarbonate foam article as claimed in claim 18, in which additional volatile solvents are added to the reactants.

24. A method of making a biostable polycarbonate foam article as claimed in claim 18, in which solubilized carbon dioxide is added to the reactants.

25. A method of making a biostable polycarbonate foam article as claimed in claim 18, wherein the isocyanate can be selected from the group of aliphatic, aliphatic alicyclic, aromatic, aromatic-aliphatic diisocyanates and triisocyanates.

26. A method of making a biostable polycarbonate foam article as claimed in claim 18, in which the isocyanate is selected from one or more of p-phenylene diisocyanate, tetramethylene diisocyanate, cyclohexane 1,2-diisocyanate, m-tetramethylxylene diisocyanate, hexamethylene diisocyanate, diphenylmethane diisocyanate, 2,4-toluene diisocyanate, 2,6-toluene diisocyanate, cyclohexane-1,4-diisocyanate, isophorone diisocyanate, 4,4-dicyclohexylmethane diisocyanate and triisocyanates.

27. A biostable polycarbonate urethane article when manufactured in accordance with the method as claimed in claim 18.

28. A biostable polycarbonate urethane article as claimed in claim 27, in which the foam is first formed into a block for subsequent cutting to a desired shape.

29. A biostable polycarbonate urethane article as claimed in claim 27, wherein the article is a vascular graft, septal defect occluder, vessel occluder, vessel defect occluder, mammary prosthesis, pacemaker lead, embolic filter, LVAD bladder, a probe, a cannula, or catheter.

* * * * *